United States Patent
Bhattacharya et al.

(10) Patent No.: US 7,807,195 B2
(45) Date of Patent: Oct. 5, 2010

(54) EXTENDED RELEASE FORMULATION OF VENLAFAXINE HYDROCHLORIDE

(75) Inventors: Sampad Bhattacharya, Vadodara (IN); Rajesh Kshirsagar, Vadodara (IN); Mayank Joshi, Vadodara (IN); Sandeep Pandita, Vadodara (IN)

(73) Assignee: Alembic Limited, Gujarat Vadodara (IN)

( * ) Notice: Subject to any disclaimer, the term of this patent is extended or adjusted under 35 U.S.C. 154(b) by 1155 days.

(21) Appl. No.: 11/031,266

(22) Filed: Jan. 7, 2005

(65) Prior Publication Data

US 2005/0169985 A1 Aug. 4, 2005

(30) Foreign Application Priority Data

Feb. 4, 2004 (IN) .................. 117/MUM/2004
Sep. 13, 2004 (IN) .................. 980/MUM/2004

(51) Int. Cl.
*A61K 9/64* (2006.01)
*A61K 9/52* (2006.01)
*A61K 9/20* (2006.01)

(52) U.S. Cl. .................. 424/458; 424/456; 424/457

(58) Field of Classification Search .................. 424/457
See application file for complete search history.

(56) References Cited

U.S. PATENT DOCUMENTS

| 4,153,677 | A | * | 5/1979 | John | .................. 424/495 |
| 4,535,186 | A | | 8/1985 | Husbands | |
| 6,274,171 | B1 | | 8/2001 | Sherman | |
| 6,346,269 | B1 | * | 2/2002 | Hsiao et al. | .................. 424/472 |
| 6,696,496 | B2 | * | 2/2004 | Oosterbaan et al. | ......... 514/648 |
| 6,703,044 | B1 | * | 3/2004 | Pinhasi et al. | ............... 424/452 |
| 7,309,719 | B1 | * | 12/2007 | Aomatsu | .................. 514/561 |
| 2002/0155156 | A1 | * | 10/2002 | Mulye | .................. 424/482 |
| 2003/0133982 | A1 | | 7/2003 | Heimlich et al. | |
| 2003/0190354 | A1 | | 10/2003 | Sela | |
| 2004/0096501 | A1 | | 5/2004 | Vaya | |
| 2006/0257482 | A1 | * | 11/2006 | Kumar et al. | ............... 424/469 |

FOREIGN PATENT DOCUMENTS

| EP | 0797991 | | 10/1997 |
| WO | WO 94/27589 | | 12/1994 |
| WO | WO 99/22724 | | 5/1999 |
| WO | WO 01/37815 | A1 | 5/2001 |
| WO | WO 03/053402 | A1 | 7/2003 |
| WO | WO 03/055475 | A1 | 7/2003 |
| WO | WO 2004/012699 | A2 | 2/2004 |

* cited by examiner

*Primary Examiner*—Lakshmi S Channavajjala
*Assistant Examiner*—Rachael E Welter
(74) *Attorney, Agent, or Firm*—Akerman Senterfitt; Peter A. Chiabotti

(57) ABSTRACT

The present invention relates to an extended release once daily pharmaceutical formulation comprising venlafaxine hydrochloride and pharmaceutically acceptable excipients. More particularly, the present invention relates to an extended release composition in the form of mini-tablets which are incorporated in hard gelatin capsules.

3 Claims, 1 Drawing Sheet

EXTENDED RELEASE FORMULATION OF VENLAFAXINE HYDROCHLORIDE

BACKGROUND OF THE INVENTION

1. Field of the Invention

This invention relates to a pharmaceutical composition of extended release formulation comprising hard gelatin capsule containing therapeutically effective amount of mini-tablets wherein each mini-tablet comprises venlafaxine hydrochloride, microcrystalline cellulose, binder and optionally conventional excipients.

2. Related Art of the Invention

The use of hydrophobic polymers to produce extended or controlled release pharmaceutical composition is known in the art. For extending the release, the solid dosage form of mini-tablets comprising a drug is coated with hydrophobic polymer and pore forming agent. As soon as solid dosage form comes in contact with surrounding media, the pores are formed and the drug is diffused through these pores. Control of the rate of release benefits therapy by producing constant blood plasma levels of the active ingredient and by decreasing the frequency of administration, thereby improving patient compliance to the dosage regimen. The present invention provides a pharmaceutical composition of extended release capsule containing mini-tablets of venlafaxine hydrochloride suitable for once daily administration to human subjects.

The invention relates to an extended release pharmaceutical formulation for once daily administration, in particular to a controlled release pharmaceutical formulation of venlafaxine hydrochloride.

Several extended release drug delivery system adapted for the delivery of venlafaxine hydrochloride are known in the prior art.

U.S. Pat. No. 4,535,186 describes a class of hydroxycycloalkanephenethyl amines as being useful antidepressants and exemplifies the compound now known as venlafaxine hydrochloride as one of the suitable species.

Venlafaxine, is chemically named as (R/S)-1-[2-(dimethylamino)-1-(4-methoxyphenyl)ethyl]-cyclohexanol. Presently venlafaxine hydrochloride is administered to adults as conventional immediate release tablets or as 24 hours extended-release multiparticulate capsules. Venlafaxine hydrochloride is approved for sale in various countries including the United States of America under the brand name EFFEXOR™ (Wyeth Ayerst). It is available as an immediate release tablet and as an extended release capsule under the brand name EFFEXOR™ (Wyeth Ayerst) and EFFEXOR XR™ (Wyeth Ayerst), respectively.

Venlafaxine hydrochloride is very soluble in water. It is known that it is very difficult to develop a pharmaceutical form with a very slow dissolution rate of freely soluble drug.

U.S. Pat. No. 6,274,171 and related EP 0797991 disclose encapsulated extended release formulations form venlafaxine hydrochloride. A once daily, encapsulated extended release dosage form is disclosed that provides a flattened drug plasma profile and reduces the adverse side effects. The encapsulated dosage form is taught to comprise spheroids of venlafaxine hydrochloride, microcrystalline cellulose, and hydroxypropylmethylcellulose (HPMC). These spheroids are coated with a mixture of ethyl cellulose and HPMC. By providing an appropriate amount of the coating, the desired blood plasma profile can be obtained.

U.S. Pat. No. 6,274,171 and EP 0797991 also state that forming an extended release dosage from of venlafaxine hydrochloride was difficult in part due to the high water solubility of the hydrochloride salt. In fact, these patents disclose that "[n]umerous attempts to produce extended release tablets by hydrogel technology proved to be fruitless because the compressed tablets were either physically unstable (poor compressibility or capping problems) or dissolved too rapidly in dissolution studies." Unlike the encapsulated extended release formulations described in these patents, a hydrogel extended release venlafaxine hydrochloride tablet is taught to typically exhibit a dissolution profile wherein 40%-50% is released within 2 hours, 60%-70% is released within 4 hours, and 85%-100% is released within 8 hours.

WO99/22724 also discloses encapsulated venlafaxine hydrochloride extended release dosage forms. These formulations differ from those in U.S. Pat. No. 6,274,171 and EP 0797991 in that the spheroid is substantially free of HPMC.

Although a venlafaxine extended release capsule has been produced, it would be advantageous to provide a less complicated dosage form that nonetheless provides extended release of venlafaxine.

WO94/27589 and WO01/37815 describe osmotic dosage forms containing venlafaxine hydrochloride.

US 20030190354 discloses an extended release composition comprising as active compound venlafaxine hydrochloride in a matrix tablet dosage form, in which venlafaxine hydrochloride is mixed with a combination of hydrophilic and hydrophobic matrix forming components. The matrix components are suitably combination of high and low viscosity grades hydroxyl propyl methyl cellulose, ethyl cellulose, glyceryl behenate and methyl cellulose. Two granulation methods were used for the production of the tablets: the first was a regular one step granulation process, in which all excipients were blended together with the active, then wet granulated with Kollidon SR, dried, milled and compressed into oval shape scored tablets. The second granulation process was a two step process, the first was wet granulation of the active material, which was blended with the hydrophobic components selected from Ethocel or Compritol. Later on, the milled granulate was mixed with the hydrophilic components, the methocels and the lubricating components, syloid 244 and Mg stearate.

WO03/55475 teaches the controlled release formulation of venlafaxine. The pharmaceutical formulation of the present invention comprises for example a core consisting of an active drug which may be advantageously in amorphous form, polyvinylpyrrolidone, a combination of two hydrophilic polymers having different viscosity and optionally other commonly used ingredients for solid dosage forms. The core is coated with a polymeric coating comprising a combination of two polymers having different water permeability. A plasticizer and other commonly used ingredients for film coating may be optionally added thereto. The combination of the carriers i.e. the water soluble polymer, polyvinylpyrrolidone and the low viscosity hydrophilic polymer has a double effect and the advantage that it stabilizes the amorphous form of the active ingredient and simultaneously modifies the release of the amorphous active ingredient in such a way that it is sustained, repeatable and independent of the amorphous or polymorphous form of the active ingredient, its particle size and specific surface area.

WO 03/53402 and related US 2004133982 discloses zero-order sustained release dosage forms. A solid dosage form comprising a matrix core comprising intragranular ethylcellulose and a water soluble active agent granulated and compressed together with extragranular ethyl cellulose and a film coating comprising a hydrophobic polymer wherein the film coating completely encases the matrix core. This invention also relates to a process for manufacturing a zero-order sustained release tablet containing a water-soluble active agent, comprising the steps of: (a) preparing a first admixture comprising the active agent and intragranular ethylcellulose; (b) granulating the first admixture in order to obtain a granular product; (c) preparing a second admixture comprising extragranular ethylcellulose; (d) preparing a third admixture comprising the granular product and the second admixture;

WO04/12699 and related US 20040096501 teach the use of dual retard technique to effectively control the release rate of modified release active ingredient by using small quantity of release controlling agents. This dual retard technique thus sufficiently reduces the size of the dosage form, which is convenient for swallowing. The dosage form comprises of a) Micro matrix particles containing high solubility active ingredient and one or more hydrophobic release controlling agent, b) Coating of Micro matrix particles with one or more hydrophobic release controlling agents.

Extended release preparation of drugs are advantageous in the administration because of their reduced dosage frequency. The frequency can be reduced by maintaining constant plasma concentration of drug over an extended period of time to ensure extended effect of active ingredient.

SUMMARY OF THE INVENTION

It is an object of the present invention to provide an extended release of the active ingredient from the pharmaceutical composition, which has blood plasma levels above minimum therapeutic concentration over extended period of time.

Another object of the present invention is to provide extended release pharmaceutical composition for once daily dosage form.

Yet another object of the present invention is to provide an extended release pharmaceutical composition, which releases the active ingredient in predetermined manner.

Yet another object of the present invention is to produce the formulation by a conventional method so as to reduce the process time.

Yet another object of the present invention is to develop extended release formulation of venlafaxine hydrochloride which is bioequivalent to Effexor XR by conventional method comprising compression and coating.

Accordingly, the present invention relates to an extended release pharmaceutical formulation comprising venlafaxine hydrochloride, diluent, water-soluble component and water insoluble polymer and other pharmaceutical acceptable excipients.

The components are selected in such a way to give extended release of the venlafaxine hydrochloride in a predetermined manner.

The invention relates to extended release composition in the form of mini-tablets which are incorporated in hard gelatin capsules containing a therapeutically effective amount of the mini-tablets comprised of venlafaxine hydrochloride, microcrystalline cellulose, polyvinyl pyrrolidone and optionally conventional excipients and further coating of mini-tablets comprising of ethyl cellulose and plasdone S630 copolyvidonium (ISP technologies). The tablets of the invention exhibit specific dissolution profiles, especially with venlafaxine HCl.

Preferably, the present invention relates to the extended release formulation which comprises from about 40% to about 80% by weight of a venlafaxine hydrochloride; from about 25% to about 45% of microcrystalline cellulose and from about 0.5% to about 10% polyvinyl pyrrolidone of the total weight of composition. The coating on mini-tablet comprises of from about 2% to 15% of total weight of the composition. The coating composition comprises from about 50% to about 95% ethylcellulose and from about 3% to about 50% of plasdone S-630 copolyvidonium (ISP technologies) of the total weight of the coating layer.

More preferably the present invention relates to the extended release formulation which comprises from about 48% to about 68% by weight of a venlafaxine hydrochloride; from about 26% to about 38% of microcrystalline cellulose and from about 2% to about 9% of polyvinyl pyrrolidone of the total weight of composition. The coating on mini-tablet comprises of from about 4% to 14% of total weight of the composition. The coating on mini-tablet comprises of from about 65% to about 95% ethylcellulose and from about 5% to about 40% of plasdone S-630 copolyvidonium of the total weight of the coating layer.

Still more preferably the present invention relates to the extended release formulation which comprises from about 57% to about 62% by weight of a venlafaxine hydrochloride; from about 27% to about 32% of microcrystalline cellulose and from about 2.5% to about 5.5% of polyvinyl pyrrolidone of the total weight of composition. The coating on mini-tablet comprises of from about 6% to 12% of total weight of the composition. The coating on mini-tablet comprises of from about 70% to about 80% ethylcellulose and from about 20% to about 30% of plasdone S-630 copolyvidonium of the total weight of the coating layer.

BRIEF DESCRIPTION OF THE INVENTION

According to the present invention, the extended release formulation is prepared by compression followed by functional coating method, the said method comprising steps of:

i. Blending the venlafaxine hydrochloride and diluent.

ii. Granulating the blended mixture with an aqueous or non-aqueous solution of binder and drying it.

iii. Lubricating the dried granules and compressing into tablets of appropriate shape (3-6 mm in diameter).

iv. Coating the tablets with an aqueous or non-aqueous dispersion of water insoluble and water soluble polymer.

v. Filling coated mini tablets obtained in step (iv) into capsule of appropriate size.

Such 12, 6, 3 mini-tablets are filled into pharmaceutically acceptable capsule to form 150 mg, 75 mg and 37.5 mg strengths respectively of venlafaxine.

DETAILED DESCRIPTION OF THE INVENTION

Figure 1:
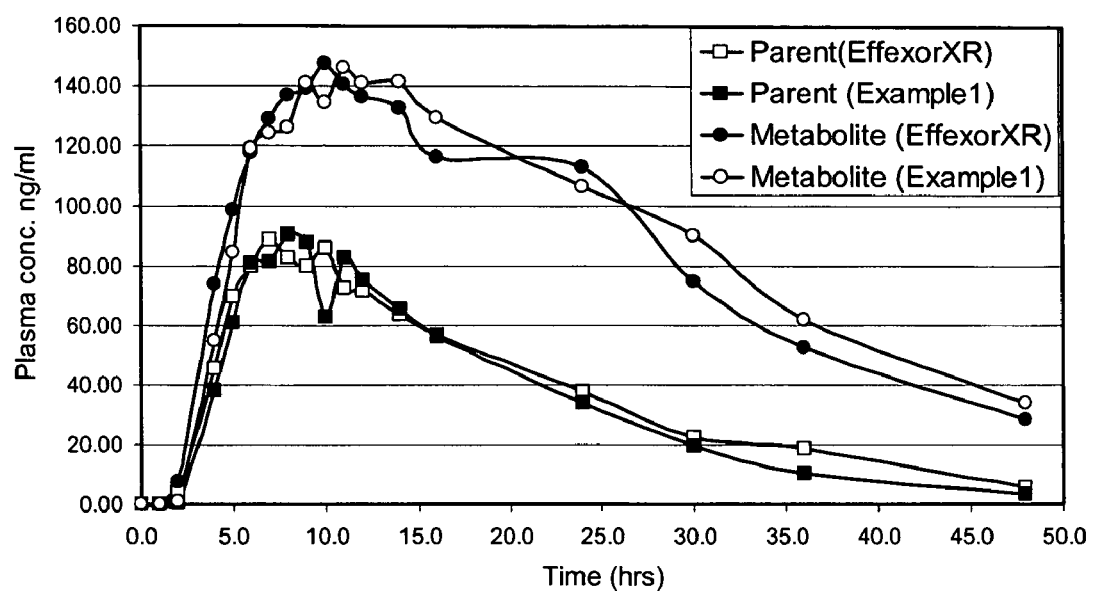
FIG. 1 is a plot of the mean drug plasma level resulting from the biopharmaceutical test comparing Example 1 to venlafaxine hydrochloride 150 mg (Effexor XR™), of which the pharmacokinetic parameters are recorded in Table 1.

In an embodiment of the present invention, the hard gelatin capsule comprises of film coated mini-tablets. These mini-tablets comprised of active ingredient, binder and water-soluble component and optionally conventional excipients. These mini-tablets are coated with combination of water-soluble and waters insoluble polymer.

According to the present invention, the pharmaceutical composition contains venlafaxine hydrochloride as an active ingredient. The venlafaxine hydrochloride may be present in an amount from about 40% to about 80%, preferably from about 48% to about 68% by weight, more preferably from about 57% to about 62% of the total weight of extended release composition.

Further, venlafaxine hydrochloride may be present in an amount from 12.5 mg to 400 mg per capsule.

According to the embodiment of the present invention, the mini-tablet contains microcrystalline cellulose as diluent. Microcrystalline cellulose may be present in an amount from about 25% to about 45%, preferably from about 26% to about 38% by weight, more preferably from about 27% to about 32% of the total weight of extended release composition.

According to the embodiment of the present invention, the mini-tablet contains polyvinyl pyrrolidone as binder. Polyvinyl pyrrolidone may be present in an amount from about 0.5% to about 10%, preferably from about 2% to about 9% by weight, more preferably from about 2.5% to about 5.5% of the total weight of extended release composition.

In addition to the above ingredients, pharmaceutical grade magnesium stearate/stearic acid as a glidant, talc as an antiadherent and colloidal silicion dioxide as a lubricant are included in the mini-tablet. Preferably, magnesium stearate/stearic acid, talc and colloidal silicion dioxide are present in amounts in the range of 1% to 6% by weight either alone or in combination.

In an embodiment of the present invention, the coating on mini-tablet comprises of water insoluble polymer and water-soluble polymer. The water insoluble polymer is selected from the group consisting of cellulose ether such as ethylcellulose, a cellulose ester such as cellulose acetate, methacrylic derivatives available from Rohm Pharma under the trade name "Eudragit™" RL, RS and NE, etc. In a preferred embodiment, the water insoluble polymer is ethyl cellulose present in an amount from about 50% to about 95% by weight of the functional coating content of extended release composition.

In an embodiment of the present invention, the coating on mini-tablet also contains water-soluble polymer. The water soluble polymer is selected from the group consisting of Plasdone S-630 copolyvidonum (ISP technologies), hydrated colloidal silica, sucrose, mannitol or any other substance capable of playing the same role. In preferred embodiment, the water soluble polymer is Plasdone S-630 copolyvidonum (ISP technologies) which is present in an amount from about 3% to about 50% by weight of the functional coating content of extended release composition.

Ethyl cellulose, an ethyl ether of cellulose, is a long-chain polymer of b-anhydroglucose units joined together by acetal linkages. It is tasteless, free flowing, white to light tan colored powder. It is a stable, slightly hygroscopic material. It is practically insoluble in glycerin, propylene glycol and water. Ethylcellulose that contains less than 46.5% of ethoxyl groups is freely soluble in chloroform, methyl acetate and tetrahydrofuran and in mixtures of aromatic hydrocarbons with ethanol (95%). Ethylcellulose that contains not less than 46.5% of ethoxy groups is freely soluble in chloroform, ethanol (95%), ethyl acetate, methanol and toluene. It is chemically resistant to alkalis, both dilute and concentrated and to salt solutions, although it is more sensitive to acidic materials than are cellulose esters. Ethyl cellulose polymers exhibit good stability within the pH range of 3 to 11, so they can be used with both acidic and alkaline ingredients.

The viscosity of ethyl cellulose is measured typically at 25° C. using 5% w/v ethylcellulose dissolved in a solvent blend of 80% toluene: 20% ethanol (w/w). Different grades of ethylcellulose are ethocel std 4 premium, ethocel std 7FP premium, ethocel std 7 premium, ethocel std 10FP premium, ethocel std 10P premium, ethocel std 20P premium, ethocel std 45P premium, ethocel std 100FP premium, ethocel 100P having viscosity range of 3-5.5 cP, 6-8 cP, 6-8 cP, 9-11 cP, 9-11 cP, 18-22 cP, 41-49 cP, 90-110 cP, 90-110 cP respectively. The viscosity of an ethylcellulose solution increases with an increase in ethylcellulose concentration. The viscosity of such solutions depends almost entirely on the alcohol content and is independent of toluene. In addition, nonpharmaceutical grades of ethylcellulose that differ in their ethoxyl content and degree of polymerization are available. Ethyl cellulose is prepared by treating purified cellulose with an alkaline solution, followed by ethylation of the alkali cellulose with chloroethane.

Plasdone S-630 copolyvidonum (ISP technologies) is a synthetic water-soluble copolymer consisting of N-vinyl-2-pyrrolidone and vinyl acetate in a random 60:40 ratio. Plasdone S-630 copolyvidonum has low hygroscopicity. At 50% RH level, Plasdone S-630 copolyvidonum gains less than 10% weight and does easily desorb the gained moisture. It is an excipient of choice for moisture sensitive drugs.

The K-value for Plasdone S-630 copolyvidonum is specified between 25.4 and 34.2. The K-value is calculated from the kinematic viscosity of a 1% aqueous solution and hence is related to the average molecular weight of the polymer.

Plasdone S-630 copolyvidonum is a highly effective film forming adhesive. It is used primarily as a tablet binder, although its unique properties make it useful in the formulation and coating of a variety of pharmaceutical dosage forms.

Plasdone S-630 copolyvidonum is soluble in many solvents and can be used in non-aqueous granulation or coatings. It is supplied as a free-flowing spray-dried powder to ensure maximum handling efficiency. Spray drying results in spherical particles with tightly controlled particle size distribution. The particle morphology is responsible for the excellent powder flow properties, which aids blending with other excipients.

According to a process for making the composition of the present invention, the venlafaxine hydrochloride is blended with microcrystalline cellulose and granulated using binder solution. These granules are then compressed into mini-tablets. The resulting mini-tablets are then coated with extended release polymer.

In an embodiment of the present invention, the functional coating is done by dissolving ethylcellulose and plasdone S 630 copolyvidonum in a solvent such as ethyl alcohol. The resulting solution is sprayed onto the mini-tablet cores, using a coating pan or a perforated turbine or a fluidized bed apparatus.

In an embodiment of the present invention, the weight ratio of functional coating/tablet is comprised e.g. between 0.02 and 0.15, preferably between 0.04 and 0.14, more preferably between 0.06 and 0.12.

The mini-tablet size ranges between 3-6 mm in diameter.

Preferably, venlafaxine hydrochloride and diluent are sifted through suitable mesh sieve and the sifted mass is blended using high shear mixture and the blended mass is granulated with aqueous or non-aqueous binder solution and the granulated mass is dried until the moisture content is less than 4% w/w and the dried mass is passed through suitable mesh sieve and this granules are lubricated with lubricants, glidants, antiadherants. The lubricated granules are compressed into mini-tablets of appropriate size (3-6 mm in diameter). The mini-tablets are further coated with coating of water soluble and water insoluble polymer. These film-coated mini-tablets are filled into hard gelatin capsule.

The present invention is illustrated by the following examples.

EXAMPLES

General Procedure for the Preparation of Extended Release Capsule Containing Mini-Tablets Venlafaxine hydrochloride and microcrystalline cellulose is sifted through suitable mesh sieve and the sifted mass is blended using high shear mixture and the blended mass is granulated with aqueous polyvinyl pyrrolidone solution and the granulated mass is dried until the moisture content comes down to less than 4% w/w and the dried mass is passed through suitable mesh sieve and this granules are lubricated with magnesium stearate, colloidal silicon dioxide and talc and the lubricated granules are compressed into mini-tablets.

These mini-tablets are coated with aqueous or non-aqueous dispersion of functional coating of water soluble and water insoluble polymer. The diameter of film-coated mini-tablet ranges between 3-6 mm. These mini-tablets are then filled into hard gelatin capsule.

Such 12, 6, 3 mini-tablets are filled into pharmaceutically acceptable capsule to form 150 mg, 75 mg and 37.5 mg strengths respectively of venlafaxine hydrochloride.

Dissolution Method

For all examples, the capsule containing tablets were tested for dissolution of venlafaxine hydrochloride in 900 ml of water as dissolution media at 37° C. and in 40-mesh basket (USP Type 1) and rotated at 100 rpm.

In the following examples, the composition and its dissolution profiles are given in a tabular form.

Example 1

Composition

| Ingredient | Weight (mg/tablet) |
| --- | --- |
| Venlafaxine HCl | 14.27 |
| Microcrystalline Cellulose | 7.13 |
| Povidone | 1.10 |
| Ethyl Alcohol | q.s |
| Talc | 0.25 |
| Colloidal Silicon Dioxide | 0.25 |
| Magnesium Stearate | 0.50 |
| Ethyl Cellulose | 1.22 |
| Copolyvidone | 0.37 |
| Ethyl Alcohol | q.s. |
| Total Weight | 25.09 |

Dissolution Profile

| Time (hour) | Percent Venlafaxine HCl released |
| --- | --- |
| 1 | 0 |
| 2 | 13 |
| 4 | 38 |
| 8 | 62 |
| 12 | 75 |
| 24 | 92 |

Example 2

Composition

| Ingredient | Weight (mg/tablet) |
| --- | --- |
| Venlafaxine HCl | 14.27 |
| Microcrystalline cellulose | 7.13 |
| Povidone | 1.10 |
| Pure Water | q.s. |
| Talc | 0.25 |
| Colloidal Silicon Dioxide | 0.25 |
| Magnesium Stearate | 0.50 |
| Ethyl Cellulose | 1.59 |
| Copolyvidone | 0.48 |
| Ethyl Alcohol | q.s. |
| Total Weight | 25.57 |

Dissolution Profile

| Time (hour) | Percent Venlafaxine HCl released |
| --- | --- |
| 1 | 0.2 |
| 2 | 7.7 |
| 4 | 23.2 |
| 8 | 46.2 |
| 12 | 60 |
| 24 | 81.9 |

Example 3

Composition

| Ingredient | Weight (mg/tablet) |
| --- | --- |
| Venlafaxine HCl | 14.27 |
| Microcrystalline cellulose | 7.13 |
| Povidone | 1.10 |
| Pure Water | q.s. |
| Talc | 0.25 |
| Colloidal Silicon Dioxide | 0.25 |
| Magnesium Stearate | 0.50 |
| Ethyl Cellulose | 1.08 |
| Copolyvidone | 0.32 |
| Ethyl Alcohol | q.s. |
| Total Weight | 24.9 |

Dissolution Profile

| Time (hour) | Percent Venlafaxine HCl released |
| --- | --- |
| 1 | 6.2 |
| 2 | 22.7 |
| 4 | 48.8 |
| 8 | 77.5 |
| 12 | 92.2 |
| 24 | 102.7 |

Example 4

Composition

| Ingredient | Weight (mg/tablet) |
|---|---|
| Venlafaxine HCl | 14.27 |
| Microcrystalline cellulose | 7.13 |
| Povidone | 1.10 |
| Pure Water | q.s. |
| Talc | 0.25 |
| Colloidal Silicon Dioxide | 0.25 |
| Magnesium Stearate | 0.50 |
| Eudragit RS 30D | 3.15 |
| Talc | 0.16 |
| Triethyl Citrate | 0.19 |
| Pure Water | q.s. |
| Total Weight | 27.00 |

Dissolution Profile

| Time (hour) | Percent Venlafaxine HCl released |
|---|---|
| 1 | 8 |
| 2 | 9 |
| 4 | 12 |
| 8 | 85 |
| 12 | 104 |
| 24 | — |

Further, when the composition of the present invention was extruded, spheronized and dried to form spheroids instead of mini-tablets as envisaged in the present invention, the dissolution profile was more immediate, which is unsuitable for once daily administration, as shown in the accompanying example:

Example 5

Composition

| Sr. No. | Ingredient | Qty/Capsule (150 gm) |
|---|---|---|
|  | CORE |  |
| 1 | Venlafaxine HCl | 171.24 |
| 2 | Microcrystalline Cellulose | 85.56 |
| 3 | Povidone | 13.20 |
| 4 | Water | q.s. |
|  | COAT | 270.00 |
| 8 | Ethyl Cellulose | 19.500 |
| 9 | Copolyvidone | 5.86 |
| 10 | Ethyl Alcohol | q.s. |
|  | TOTAL WEIGHT | 295.36 |

A uniformly blended mixture of Venlafaxine Hydrochloride (171.24 g) and microcrystalline cellulose (85.56 g) was granulated into an over wetted dough using solution of povidone (13.2 g) in water. The plastic mass was extruded, spheronized and dried to prepare uncoated spheroids. The cylindrical extrudes of the composition were very sticky and fragile with variable length of the extruded cylinders which resulted into non-uniform spheroids during spheronization. The extrudes were difficult to spheronize. The formed spheroids were irregular shaped and excessively sticky in nature which resulted in the formation of aggregates. Aggregates were removed by sieving after drying the spheroids. The spheroids were further coated in a wurster type fluid bed coater with a solution of 19.5 g of Ethyl cellulose and 5.86 g of Copolyvidone in Ethyl alcohol. The fragile nature of the spheroids resulted in formation of too many fines while coating. The presence of fine bridged the formation of few aggregates during coating. The film coated spheroids were sieved to remove those aggregates and then filled into pharmaceutically acceptable capsules.

The in vitro drug dissolution studies were conducted on the formed spheroids using USP I at 37° C. and 100 rpm in 900 ml water. The drug release was as follows:

| Time (Hours) | Percent Venlafaxine HCl released |
|---|---|
| 1 | 21 |
| 2 | 84 |
| 4 | 99 |

The dissolution profile suggests that preparing spheroids of the composition claimed in the present invention would have a more immediate drug release characteristics unsuitable for once daily administration. The said invention is thus only workable for mini-tablets of diameter greater than 3 mm and not for spheroids of diameter less than 2 mm.

Biopharmaceutics:

A randomized, two treatment, two period, two sequence, single dose, crossover bioavailability study on Venlafaxine 150 mg extended release capsule (Example 1), compared with Venlafaxine hydrochloride 150 mg extended release capsule (Effexor XR™) manufactured by Wyeth Ayerst laboratories, USA, in 12 healthy, adult, male, human subjects was conducted under fasting conditions. The mean drug plasma level are shown in FIG. 1 and the pharmacokinetic parameters are recorded in Table 1.

TABLE 1

| Parameter | Unit | Parent | | Metabolite | |
|---|---|---|---|---|---|
|  |  | Example 1 | Effexor XR | Example 1 | Effexor XR |
| Cmax | ng/mL | 101.28 | 106.183 | 162.33 | 166.025 |
| Tmax | h | 7.67 | 8.500 | 11.25 | 12.17 |
| AUC(0->t) | ng · h/mL | 1560.62 | 1669.10 | 4119.86 | 3949.95 |
| AUC(0->inf) | ng · h/mL | 1635.48 | 1823.616 | 4740.36 | 4494.14 |

The invention claimed is:

1. An extended release formulation of venlafaxine hydrochloride in the form of compressed mini-tablets having a diameter of 3-6 mm, filled in a hard gelatin capsule, said mini-tablets having a core and an outer coating, the core of said mini-tablets comprising from about 57-62% of venlafaxine hydrochloride by weight of each mini-tablet, from about 27-32% of microcrystalline cellulose by weight of each mini-tablet, and from about 2.5-5.5% of polyvinylpyrrolidone by weight of each mini-tablet, and said coating comprising (i) 70-80% of a water insoluble polymer which is selected from ethylcellulose and copolymers comprising at least two monomers selected from the group consisting of acrylic acid, methacrylic acid, esters of acrylic acid, and esters of methacrylic acid and 20-30% of a water soluble polymer which is copolyvidone, and (ii) 5-14% of the total weight of the mini-tablets, wherein said formulation exhibits the following dissolution profile when measured in a USP type I apparatus at 37° C. in water at 100 rpm:
   a) at least 46.2% of total venlafaxine hydrochloride is released at 8 hrs;
   b) at least 60% of total venlafaxine hydrochloride is released at 12 hrs; and
   c) at least 81.9% of total venlafaxine hydrochloride is released at 24 hrs.

2. The extended release formulation of venlafaxine hydrochloride according to claim 1, which is administered once daily.

3. The extended release formulation of venlafaxine according to claim 1;
   wherein the extended release formulation of venlafaxine hydrochloride is prepared by a process comprising the steps of:

(i) blending the venlafaxine hydrochloride and microcrystalline cellulose,
   (ii) granulating the blended venlafaxine hydrochloride and microcrystalline cellulose with an aqueous or non-aqueous solution of polyvinylpyrrolidone and drying it to form dried granules,
   (iii) lubricating the dried granules and compressing said granules into mini-tablets,
   (iv) coating the mini-tablets with an aqueous or non-aqueous dispersion of a water insoluble component selected from ethylcellulose and copolymers comprising at least two monomers selected from the group consisting of acrylic acid, methacrylic acid, esters of acrylic acid, and esters of methacrylic acid and a water soluble component of copolyvidone, and
   (v) filling coated mini-tablets obtained in step (iv) into capsules.

* * * * *